US010117586B1

(12) United States Patent
Mouradian et al.

(10) Patent No.: US 10,117,586 B1
(45) Date of Patent: Nov. 6, 2018

(54) CONTINUOUS NON-INVASIVE WEARABLE BLOOD PRESSURE MONITORING SYSTEM

(71) Applicant: SENSOGRAM TECHNOLOGIES, INC., Plano, TX (US)

(72) Inventors: Vahram Mouradian, Plano, TX (US); Armen Poghosyan, Yerevan (AM)

(73) Assignee: Sensogram Technologies, Inc., Plano, TX (US)

( * ) Notice: Subject to any disclaimer, the term of this patent is extended or adjusted under 35 U.S.C. 154(b) by 481 days.

(21) Appl. No.: 14/675,639

(22) Filed: Mar. 31, 2015

Related U.S. Application Data

(60) Provisional application No. 61/973,035, filed on Mar. 31, 2014.

(51) Int. Cl.
*A61B 5/05* (2006.01)
*A61B 5/021* (2006.01)
*A61B 5/00* (2006.01)

(52) U.S. Cl.
CPC ........ *A61B 5/02108* (2013.01); *A61B 5/0082* (2013.01); *A61B 5/7278* (2013.01); *A61B 2560/0223* (2013.01); *A61B 2560/0475* (2013.01); *A61B 2562/0238* (2013.01); *A61B 2576/00* (2013.01)

(58) Field of Classification Search
CPC . A61B 5/02108; A61B 5/7278; A61B 5/0082; A61B 2576/00; A61B 2562/0238; A61B 2560/0475; A61B 2560/0223
USPC .................................................. 600/473–480
See application file for complete search history.

(56) References Cited

U.S. PATENT DOCUMENTS

| 4,781,195 | A | 11/1988 | Martin |
| 5,140,990 | A | 8/1992 | Jones et al. |
| 5,447,161 | A | 9/1995 | Blazek et al. |
| 5,713,355 | A | 2/1998 | Richardson et al. |
| 5,846,190 | A | 12/1998 | Woehrle |
| 5,885,213 | A | 3/1999 | Richardson et al. |
| 5,954,644 | A | 9/1999 | Dettling et al. |
| 6,385,471 | B1 | 5/2002 | Mortz |
| 6,491,647 | B1 * | 12/2002 | Bridger .......... A61B 5/021 128/900 |
| 7,384,398 | B2 | 6/2008 | Gagnadre et al. |
| 7,616,110 | B2 | 11/2009 | Crump et al. |
| 7,740,591 | B1 | 6/2010 | Starr et al. |

(Continued)

FOREIGN PATENT DOCUMENTS

| WO | 0143624 A2 | 6/2001 |
| WO | 2008109185 A2 | 9/2008 |
| WO | 2016150749 A1 | 9/2016 |

OTHER PUBLICATIONS

International Search Report and Written Opinion for International Application No. PCT/US17/63833, dated Feb. 9, 2018, 6 pages.

(Continued)

*Primary Examiner* — Sanjay Cattungal
(74) *Attorney, Agent, or Firm* — RatnerPrestia

(57) ABSTRACT

Presented are embodiments of an apparatus and methodology integrated in the system for non-invasive, continuous, wearable, remote and mobile monitoring of human blood pressure by photoplethysmography (PPG) based sensor and an electronic processing unit with the embedded radio allowing the reading and transmittal of the read blood pressure data to the remote location.

7 Claims, 5 Drawing Sheets

(56) References Cited

U.S. PATENT DOCUMENTS

| | | | |
|---|---|---|---|
| 7,827,011 B2 | 11/2010 | De Vaul et al. | |
| 8,036,842 B2 | 10/2011 | DeVaul et al. | |
| 8,313,439 B2 | 11/2012 | McCombie et al. | |
| 8,378,811 B2 | 2/2013 | Crump et al. | |
| 8,618,930 B2 | 12/2013 | Papadopoulos et al. | |
| 8,866,606 B1 | 10/2014 | Will et al. | |
| 9,135,699 B2 | 9/2015 | Ralovich et al. | |
| 9,396,645 B2 | 7/2016 | Will et al. | |
| 9,489,815 B2 | 11/2016 | TenKate | |
| 9,526,421 B2 | 12/2016 | Papadopoulos et al. | |
| 9,547,977 B2 | 1/2017 | Will et al. | |
| 9,640,057 B1 | 5/2017 | Ross | |
| 9,704,154 B2 | 7/2017 | Xing et al. | |
| 9,773,397 B2 | 9/2017 | Ten Kate et al. | |
| 2004/0044290 A1* | 3/2004 | Ward | A61B 5/022 600/490 |
| 2009/0105556 A1* | 4/2009 | Fricke | A61B 5/0059 600/301 |
| 2009/0326386 A1 | 12/2009 | Sethi et al. | |
| 2010/0016738 A1 | 1/2010 | Addison et al. | |
| 2012/0078116 A1 | 3/2012 | Yamashita | |
| 2014/0142460 A1 | 5/2014 | Zhang et al. | |
| 2015/0164352 A1 | 6/2015 | Yoon et al. | |
| 2016/0038044 A1 | 2/2016 | Banerjee et al. | |
| 2016/0038061 A1 | 2/2016 | Kechichian et al. | |
| 2016/0174913 A1 | 6/2016 | Somanath et al. | |
| 2016/0213314 A1 | 7/2016 | Zuckerman-Stark et al. | |
| 2016/0360971 A1 | 12/2016 | Gross et al. | |
| 2017/0027511 A1 | 2/2017 | Conner | |
| 2017/0172463 A1 | 6/2017 | Papadopoulos et al. | |

OTHER PUBLICATIONS

International Search Report and Written Opinion for International Application No. PCT/US18/18159, dated May 7, 2018, 7 pages.

Addison et al., "Developing an algorithm for pulse oximetry derived respiratory rate (RRoxi): a healthy volunteer study", J. Clin. Monit Comput, 2012, vol. 26, pp. 45-51.

Image of Sensotrack, downloaded Sep. 25, 2016, 1 page.

Meredith et al., "Photoplethysmographic derivation of respiratory rate: a review of relevant physiology", Journal of Medical Engineering & Technology, 2012, pp. 60-66.

George et al., "Respiration Rate Measurement From PPG Signal Using Smart Fusion Technique", International Conference on Engineering Trends and Science & Humanities, 2015, 5 pages.

Burns, "Senso Track Monitors Biometric Health Through Your Ear", downloaded http://www.slashgear.com/sensotrack-monitors-biometric-health-through-your-ear-22351940, Sep. 25, 2016, 8 pages.

Lazaro et al., "Deriving respiration from photoplethysmographic pulse width", Med. Bio. Eng. Comput., 2013, vol. 51, pp. 233-242.

Notice of Allowance for U.S. Appl. No. 14/674,499, dated Jan. 31, 2018, 9 pages.

Notice of Allowance for U.S. Appl. No. 15/344,467, dated Jul. 9, 2018, 18 pages.

Final Office Action for U.S. Appl. No. 15/254,880, dated Aug. 27, 2018, 13 pages.

* cited by examiner

CONTINUOUS NON-INVASIVE WEARABLE BLOOD PRESSURE MONITORING SYSTEM

CROSS REFERENCE TO RELATED APPLICATIONS

This application claims the benefit of the filing date of U.S. provisional patent application Ser. No. 61/973,035, filed on Mar. 31, 2014, the disclosure of which is incorporated herein by reference for all purposes. This application is related to the commonly-owned U.S. application entitled "Apparatus for Ambient Noise Cancellation in PPG Sensors," Ser. No. 14/674,499, filed on Mar. 31, 2015, the disclosure of which is also incorporated herein by reference for all purposes.

TECHNICAL FIELD

The invention relates in general to photoplethysmographic (PPG) measurement systems and apparatuses using optical sensors, and in particular to non-invasive human blood pressure measurement by wearable optical sensing systems.

BACKGROUND INFORMATION

Photoplethysmography or photoplethysmographic (PPG) systems are typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue—where blood perfuses the tissue, and photoelectrically senses the absorption of light in such tissue. The changing light characteristics can be measured and used to determine the blood pressure of a patient and other parameters (blood oxygen saturation SpO2, respiration rate, heart rate, etc.).

Typically PPG measurement systems include an optical sensor for releasable attachment to the tip of patient's appendage (e.g., a finger, earlobe and others). The sensor directs light signals into the appendage where the sensor is attached. Some portion of light is absorbed and a remaining portion passes through patient tissue. The intensity of light passing through the tissue is monitored by a sensor. The intensity related signals produced by the sensor are used to compute blood parameters.

Blood pressure measurement techniques are generally put in two broad classes, direct and indirect. Direct techniques of blood pressure measurement, which are also known as invasive techniques, involve a catheter to be inserted in the vascular system. The indirect techniques are non-invasive, with improved patient comfort and safety, but at the expense of accuracy.

What is needed, therefore, is a blood pressure measurement technique and apparatus that is indirect and accurate.

SUMMARY

In response to these and other problems, there is disclosed a blood pressure monitoring system and method using a non-invasive device and method of monitoring it continuously. More particularly, aspects of the present invention may be a wearable non-invasive blood pressure (NIBP) monitor allowing a mobile and remote reading of blood pressure data from the close proximity as well as from the remote location via the Internet connection.

Also disclosed are aspects that include the subs-system allowing to calibrate the system to the individual user for the achievement of increased accuracy and validity.

Advantage of this invention is the ability of the system to calibrate and measure the blood pressure without any invasive equipment, allowing a comfortable wearing by the patients.

These and other features, and advantages, will be more clearly understood from the following detailed description taken in conjunction with the accompanying drawings. It is important to note the drawings are not intended to represent the only aspect of the invention.

DETAILED DESCRIPTION

Specific examples of components, signals, messages, protocols, and arrangements are described below to simplify the present disclosure. These are, of course, merely examples and are not intended to limit the invention from that described in the claims. Well known elements are presented without detailed description in order not to obscure the present invention in unnecessary detail. For the most part, details unnecessary to obtain a complete understanding of the present invention have been omitted inasmuch as such details are within the skills of persons of ordinary skill in the relevant art. Details regarding control circuitry or mechanisms used to control the rotation of the various elements described herein are omitted, as such control circuits are within the skills of persons of ordinary skill in the relevant art.

Figure 1:
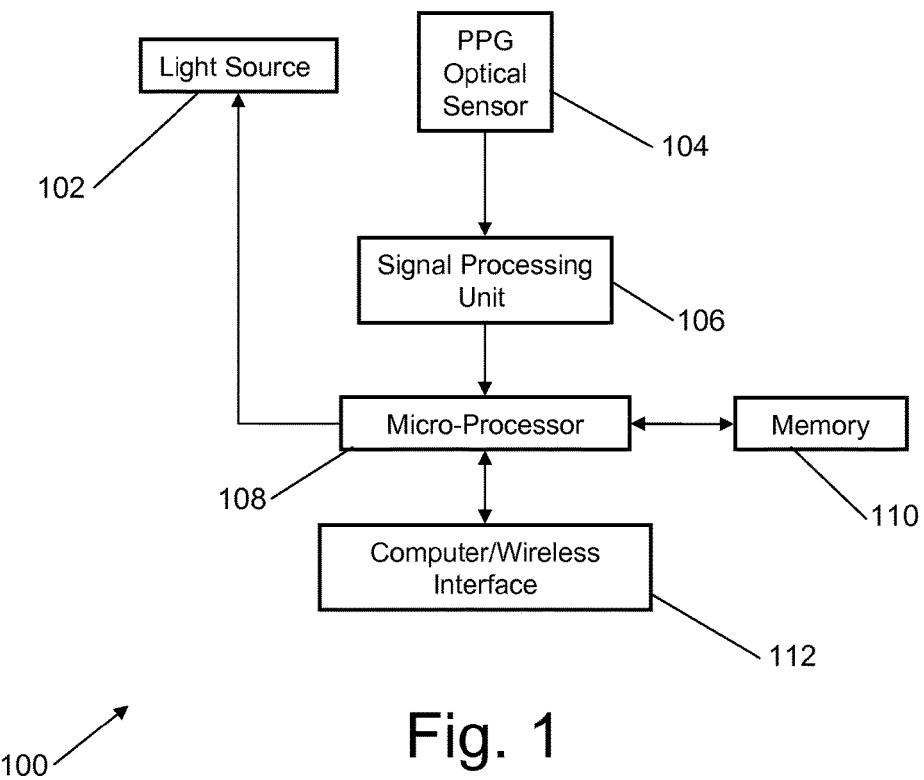
FIG. 1 is a schematic view of a system incorporating aspects of the present invention.

FIG. 1 illustrates a conceptual diagram of a non-invasive blood pressure ("NIBP") monitoring system 100. The System 100 includes a light source 102 which is adapted to shine light at human tissue. An optical sensor, such as PPG Optical sensor 104 (e.g. an infrared LED and photodiode pair for emitting light pulses into tissue of a living being, in particular a person) may be positioned to read the reflected light from the light source 102 and outputs a signal. The optical sensor 104 may be mounted on a finger, ear clip, or a watch worn by the living being.

A PPG signal processing unit 106 is adapted to receive the signal from the PPG optical sensor 104 and to communicate with a micro-processor 108. The PPG signal processing unit 106 contains instructions to reduce ambient noise in the signal and amplifies the signal thus producing a "clear" digital PPG signal (i.e., for amplifying the photodiode current into a voltage signal without ambient noises and digitizing).

The microprocessor controls the light source 102 and is coupled to a memory 110. The microprocessor also is coupled to a computer and/or wireless interface 112 which allows a user to retrieve data from the memory 110 in additional to performing other reporting and functions.

Figure 2:
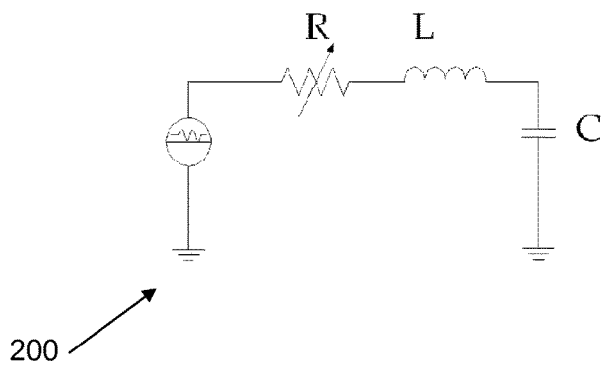
FIG. 2 shows the three-element Windkessel model which can be viewed as a description of a human cardiovascular system.

Turning now to FIG. 2, there is presented one embodiment of Windkessel non-linear 3-element RLC electrical model 200 which may be used as a basic model of human cardiovascular system, where R is the variable resistor describing whole system's Peripheral Resistance (PR), L represents the inertia of blood and C is the compliance of the vessels.

The mathematical representation of this model as a RLC circuit is presented as follows:

$$\frac{du}{dt} = R\frac{di}{dt} + L\frac{d^2i}{dt^2} + \frac{i}{C}, \quad (1)$$

then, $$u = \int \left( R\frac{di}{dt} + L\frac{d^2i}{dt^2} + \frac{i}{C} \right) dt, \quad (2)$$

where u is a function describing the blood pressure, i is the volume of the blood passing through the cross-section of the optical sensor and RLC circuit.

As will be explained below in greater detail, the optical sensor 104 is adapted to send the measured current i (i.e. PPG signal) from an infrared LED 102 to the signal processing unit 106. The PPG signal from the optical sensor 104 is processed through an ambient noise cancellation circuit and amplifier of the signal processing unit 106. The clear PPG signal is digitized and used in calculation of the blood pressure.

Figure 3:
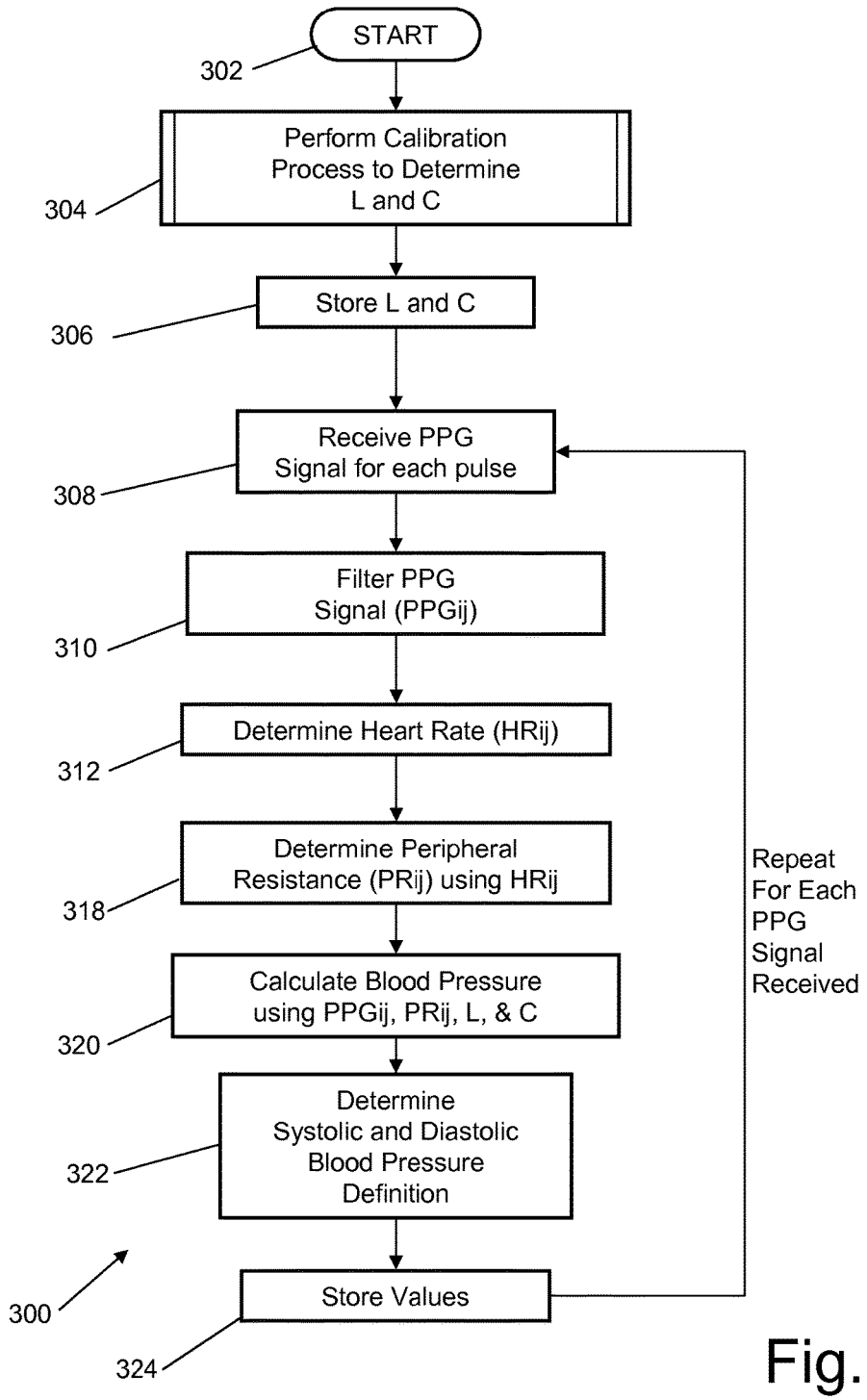
FIG. 3 is a process flow diagram which may incorporate aspects of the present invention.

FIG. 3 is a process flow chart illustrating a process which may be used with certain aspects of the present invention. The basic process starts at step 302 and continues to step 304. Step 304 represents a one-time (for individual user) L and C calibration subprocess to determine L and C based on user-specific information (measured values of systolic and diastolic blood pressures) during the one-time calibration process (described below).

For compliance C definition in step 304, it may be necessary to solve the basic equation for an averaged voltage (pressure), i.e. when the first R and second L derivatives are equal to 0.

$$\overline{u}_{av} = \frac{1}{C_i} \int_{t_i}^{t_i + 1/HR} i(t) dt \quad (3)$$

where $$\overline{u}_{av} = \frac{2 * MBP_{Dia} + MBP_{Sys}}{3} \quad (4)$$

Here $MBP_{Dia}$ and $MBP_{Sys}$ are measured diastolic and systolic blood pressures respectively. In this equation i stands for an index of interpolated data from measurement results per heart pulse lasting period. So the compliance definition starts with setting parameters of the blood pressure model as following: R=0, L=0, C=10.

As a result the calculated blood pressure signal will represent only DC component of blood pressure, which is the cause of compliance. In this description, it may be called $BP_{DCi}$. Meanwhile calculating the enabled of $BP_{DCi}$ for 30000 samples by storing in the memory 110 (FIG. 1) only those $BP_{DCi}$ values which are matching to Signal Conditioning rule. So, the compliance values are: $C_i = 10 * BP_{DCi}/u_{av}$. The compliance itself is calculated as: C=Average ($C_i$).

Inductance L definition determination may be the last process of calibration. Its predecessors are the Compliance definition and Peripheral Resistance selection. This means that at the beginning of Inductance definition already calculated C and PR needs to be set at the blood pressure model. For each period of the PPG signal the blood pressure value is calculated with the current value of $L_i$. Then the PP (Pulse Pressure=Sys−Dia) is calculated. If the calculated PP=PPM±5 (PPM is measured PP from reference device), then the current value of $L_i$ is included into array of valid L values. Then the next value of L is used for calculation, $L_{i+1} = L_i + 2$.

This process continues until the L reaches its maximum value of 50 or PP≥3/2 PPM. In the final the arithmetic average of all valid values of $L_i$ is calculated. Once the L and C have been determined in step 302, they are stored in the memory 110 (FIG. 1) for later use (step 306).

In step 308, a PPG signal is received from the PPG optical sensor 104 (FIG. 1) for processing. For purposes of this discussion, j is a data point; i is the pulse index, PPG(ij) is the blood flow gathered by PPG sensor, HR(ij) the heart rate for i-th pulse, PR(ij) is the peripheral resistance of cardiovascular system during i-th pulse, L is the blood inertia inside cardiovascular system, C is the compliance of the cardiovascular system.

In step 310, the PPG signal is processed through a ambient noise cancellation circuit of the signal processing unit 106 to produce a filtered PPG(ij) signal.

The filtered PPG(ij) signal is used by the Heart Rate determination step 312 to determine the heart rate. Step 312 uses peak detection and pulse width calculation to find the HR for each i-th pulse, then HR(ij) is generated for every j-th data points.

The HR(ij) determination is fed to Peripheral Resistance selection step 318, which uses 1D lookup table to select (interpolate/extrapolate) PR(ij) based on HR(ij). The memory 110 (FIG. 1) stores the Peripheral Resistance 1D lookup table along with the previously stored data for L and C.

In step 320, the blood pressure can be calculated using the previously processed value PPG(ij) and the selected PR(ij), L and C values to compute the continuous blood pressure.

The continuous blood pressure is used by step 322 to determine the Systolic and Diastolic blood pressure definition, where all values are stored in the memory 110 (FIG. 1) for additional processing and reporting.

Because this is a continuous process, the process then flows back to step 308 where a new PPG signal corresponding to the next pulse (or period) is received and the process flows to step 310 where the steps are repeated.

Figure 4:
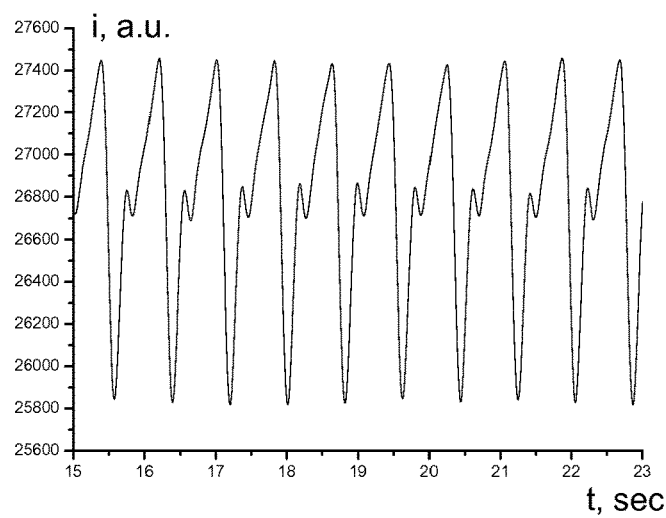
FIG. 4 shows a clear PPG signal obtained from the optical sensor.
Figure 5:
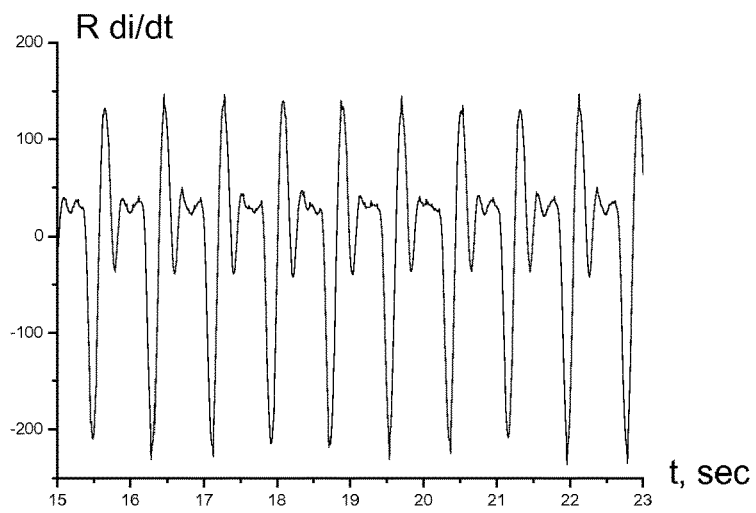
FIG. 5 shows the first derivative of PPG signal of FIG. 4.
Figure 6:
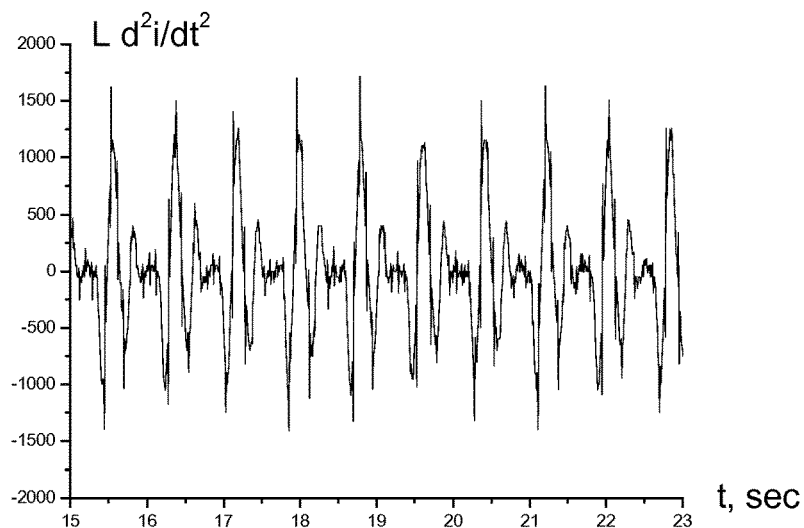
FIG. 6 shows the second derivative of PPG signal of FIG. 4.
Figure 7:
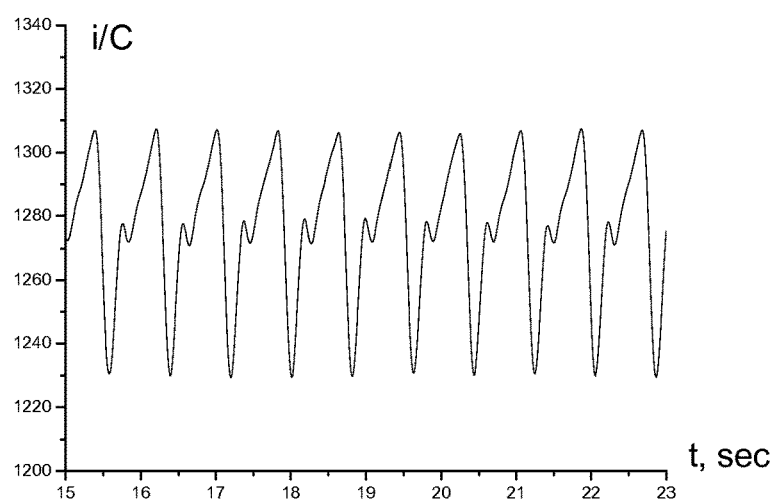
FIG. 7 is chart corresponding the ratio of the volume of the blood passing through the cross-section of an optical sensor and RLC circuit to compliance of vessels (vertical axis) over time (horizontal axis).
Figure 8:
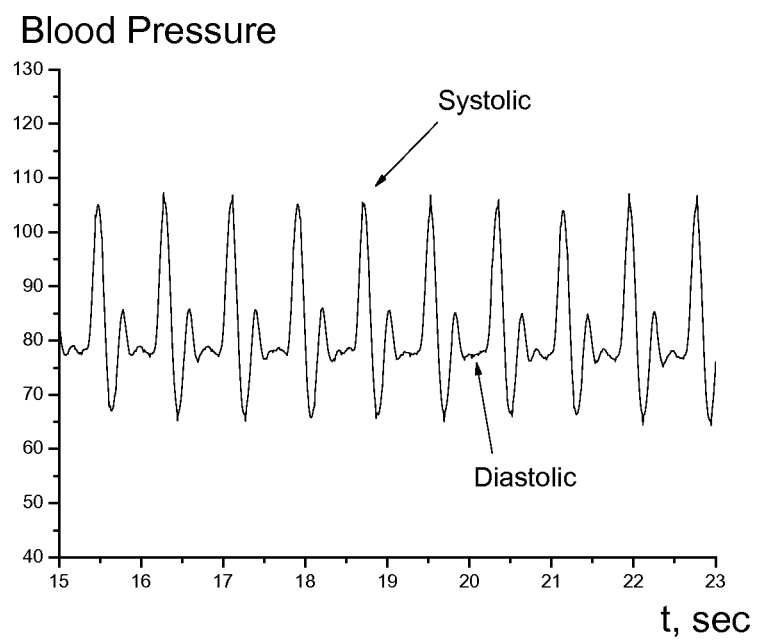
FIG. 8 shows the continuous blood pressure dependence to calculate the diastolic and systolic blood pressures.

FIG. 4 is a graph illustrating a clear PPG(ij) signal obtained from the optical sensor 104. FIGS. 5-7 show waveforms in various stages corresponding to the different components of the equation (1) discussed above. FIG. 8 shows the continuous blood pressure dependence which is used for calculation of the diastolic and systolic blood pressures.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112, paragraph 6. Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word means are not intended to fall under 35 USC 112, paragraph 6.

The foregoing description of the embodiments of the invention has been presented for the purposes of illustration and description. It is not intended to be exhaustive or to limit the invention to the precise form disclosed. Many combinations, modifications and variations are possible in light of the above teaching. For instance, in certain embodiments, each of the above described components and features may be individually or sequentially combined with other components or features and still be within the scope of the present invention. Undescribed embodiments which have interchanged components are still within the scope of the present invention. It is intended that the scope of the invention be limited not by this detailed description, but rather by the claims.

What is claimed is:

1. A method of continuously monitoring blood pressure, the method comprising:
    (a) performing a calibration sub-process to determine and store inductance (L) and compliance of the cardiovascular system (C) for each individual user;
    (b) retrieving the stored values for L and C;
    (c) receiving a photoplethysmographic (PPG) signal for each pulse or for a given time period;
    (d) filtering the received PPG signal to produce a clean PPG signal;
    (e) determining the heart rate;
    (f) determining the peripheral resistance using the heart rate;
    (g) calculating the blood pressure using the clean PPG signal, the peripheral resistance, L and C; and
    (h) determining the systolic and diastolic blood pressure.

2. The method of claim 1, further comprising repeating steps (b) through (h) for each predetermined time period.

3. The method of claim 1, further comprising repeating steps (b) through (h) for each pulse of a user.

4. The method of claim 1, further comprising storing the systolic and diastolic blood pressure in a memory.

5. A system for continuously monitoring blood pressure, the system comprising:
    a light source;
    an optical sensor positioned to receive reflected light from the light source;
    a signal processing unit adapted to receive an electrical signal from the optical sensor and configured to output a clean digital signal;
    a microprocessor in communication with the light source, the signal processing unit, a memory and a computer/wireless interface, the microprocessor having instructions for:
        (a) performing a calibration sub-process to determine and store inductance (L) and compliance of the cardiovascular system (C) for each individual user;
        (b) retrieving the stored values for L and C;
        (c) receiving a photoplethysmographic (PPG) signal for each pulse or for a given time period;
        (d) filtering the received PPG signal to produce a clean PPG signal;
        (e) determining the heart rate;
        (f) determining the peripheral resistance using the heart rate;
        (g) calculating the blood pressure using the clean PPG signal, the peripheral resistance, L and C; and
        (h) determining the systolic and diastolic blood pressure.

6. The method of claim 5, further comprising repeating instructions (b) through (h) for each predetermined time period.

7. The method of claim 5, further comprising repeating instructions (b) through (h) for each pulse of a user.

* * * * *